(12) United States Patent
Scholly et al.

(10) Patent No.: US 8,128,557 B2
(45) Date of Patent: Mar. 6, 2012

(54) ENDOSCOPE WITH HEAT DISSIPATING HANDLE

(75) Inventors: Werner Scholly, Denzlingen (DE); Stefan Schlenker, Freiburg (DE); Steffen Paul, Freiburg (DE); Volker Grimmig, Freiburg (DE)

(73) Assignee: Schölly Fiberoptic GmbH, Denzlingen (DE)

( * ) Notice: Subject to any disclaimer, the term of this patent is extended or adjusted under 35 U.S.C. 154(b) by 890 days.

(21) Appl. No.: 12/170,541

(22) Filed: Jul. 10, 2008

(65) Prior Publication Data

US 2009/0018397 A1  Jan. 15, 2009

(30) Foreign Application Priority Data

Jul. 11, 2007 (DE) .................. 10 2007 032 200

(51) Int. Cl.
*A61B 1/00* (2006.01)
*A61B 1/06* (2006.01)

(52) U.S. Cl. ........ 600/131; 600/112; 600/136; 600/178; 600/179

(58) Field of Classification Search .................. 600/112, 600/131, 136, 178, 179
See application file for complete search history.

(56) References Cited

U.S. PATENT DOCUMENTS

| | | | |
|---|---|---|---|
| 6,004,263 A * | 12/1999 | Nakaichi et al. | 600/176 |
| 2002/0120181 A1* | 8/2002 | Irion | 600/178 |
| 2006/0173245 A1* | 8/2006 | Todd et al. | 600/178 |
| 2006/0183977 A1* | 8/2006 | Ishigami et al. | 600/179 |
| 2007/0123752 A1* | 5/2007 | Melanson | 600/182 |
| 2011/0193948 A1* | 8/2011 | Amling et al. | 348/68 |

* cited by examiner

*Primary Examiner* — John P Leubecker
*Assistant Examiner* — Arnaldo Torres Diaz
(74) *Attorney, Agent, or Firm* — Volpe and Koenig, P.C.

(57) ABSTRACT

An endoscope (1) is provided having a handle (2) and a probe part (3) that can be connected thereto, with an illumination system comprising at least one light emitting diode (6) and a video system having an image receiver being arranged in the handle (2). A carrier element (12) made of a heat-conducting material is provided for at least one light emitting diode (6) inside the handle (2), to which the light emitting diode (6) is directly connected. The carrier element thermally contacts the housing parts and/or installation parts of the handle (2) and the probe part (3) for heat conductivity and/or dissipation.

6 Claims, 2 Drawing Sheets

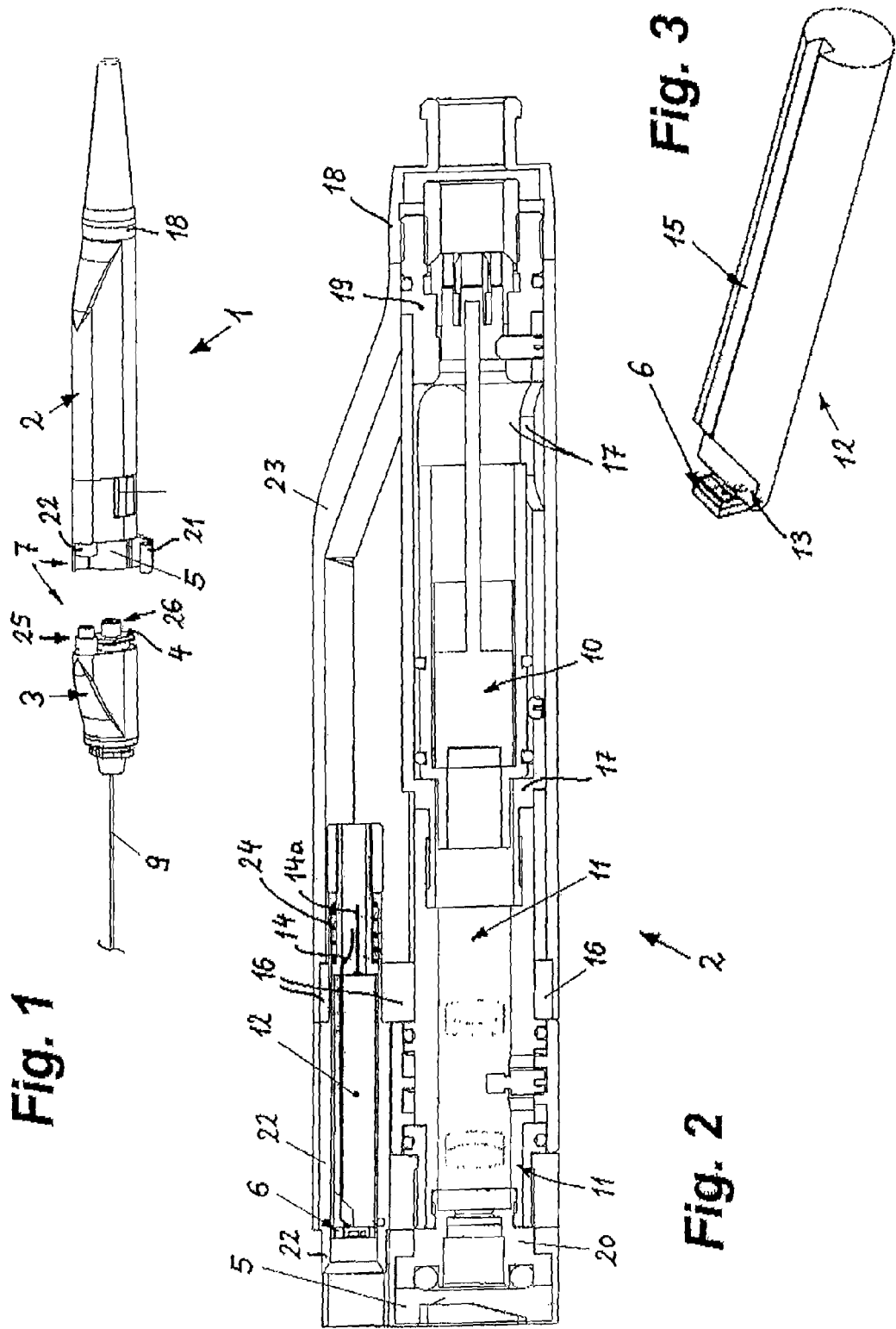

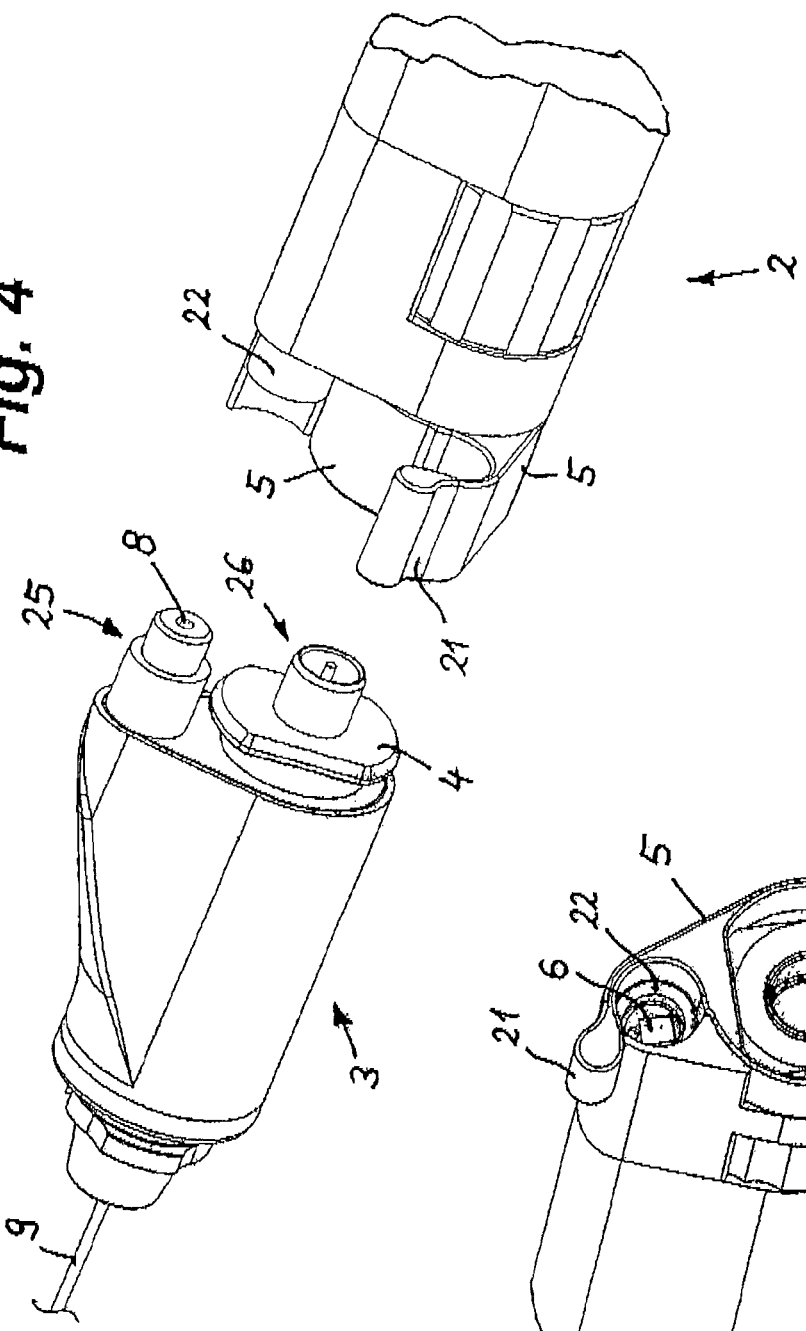

ENDOSCOPE WITH HEAT DISSIPATING HANDLE

BACKGROUND

The invention relates to an endoscope having a handle as well as a probe part that can be connected thereto, with at least one light emitting diode as well as a video system having an image receiver arranged in the handle, with a carrier element comprising a heat conducting material being provided for the at least one light emitting diode inside the handle directly connected to the light emitting diode, and with the carrier element being in a thermal contact to housing parts and/or installation parts of the handle and the probe part, if applicable.

An endoscope is known from US 2002/0120181 A1, which is provided with an illumination system inside its handle that can be connected to a probe part. In the handle of endoscopes of prior art, perhaps having an optic lens arrangement or a video system with an image receiver, several LED-light emitting diodes are provided for this purpose, with their light beams being deflected via corresponding prisms to a light conductor, which leads to the distal end of the endoscope. However, the deflection of the light beams emitted by the light emitting diodes via the prisms requires a considerable amount of space inside the handle and additionally this deflection is connected to a loss of luminous power which may only be negligible when several light emitting diodes are used. The use of several light emitting diodes is disadvantageous, though, in that this may result in a corresponding increase in heat developing inside the handle.

In such endoscopes, only electric feed lines for the illumination system and the video system are necessary, so that the handling of the endoscope is facilitated even in very small designs and thus is practically not interfered with by the feed lines.

In an illumination source integrated in the handle it is problematic that a comparatively high localized heat develops, which heats the handle, causing the manual holding to be potentially compromised. Additionally, the installation parts of the handle, particularly the camera with the image receiver and additional electronic components, as well as the lens unit with the adhesives in the optic device are subject to high thermal load, here.

When using a high-performance light emitting diode, LED for short, a temperature develops immediately at the LED-chip which is not permissible in medical devices, particularly endoscopes.

Therefore, an endoscope of the type noted at the outset is provided, which has a handle as well as a probe part that can be connected thereto (cf. EP 1 875 853 A1). In the handle of the known endoscope an illumination system with a light emitting diode is integrated in addition to a video system with an image receiver. Here, the light emitting diode is placed at a penetrating opening which is arranged in a cylindrical carrier element comprising a heat conducting material. This carrier element is held inside the handle at semi-cylindrical frame parts connected to each other in the longitudinal direction, which are also produced from heat-conducting material and are mounted at the interior perimeter of the handle.

A comparable endoscope is also known from EP 1 880 660 A1. The latter publications relate to patent publications with earlier filing dates but later publication dates.

SUMMARY

Therefore the object of the invention is to provide an endoscope of the type noted at the outset which is not subject to an overall impermissible heating even when light sources are used with a high localized heat development and with its installation parts being subject to a comparatively low temperature load.

The object according to of the invention is attained in the endoscope mentioned at the outset, particularly such that the carrier element is embodied rod-shaped and extends from the installation site of the light emitting diode to the rear part of the handle to such an extent that a sufficient dissipation and cooling surface is formed to cool the light emitting diode so that the volume and/or the surface of all thermally conducting elements serve to dissipate heat and cool the light emitting diode (6) via the at least one light emitting diode with one pole of its electric connectors being connected to the carrier element (12). A holder is provided as a heat bridging part, being in a thermal contact to the carrier element and a lens cartridge, and a coupling with bayonet-like engaging coupling parts is provided between the handle and the probe part, which coupling parts are in a thermal contact to the carrier element of the light emitting diode via a holding plate and the holder acts as the heat bridging part.

In the endoscope according to the invention at least one light emitting diode is connected to the carrier element with one pole of its electric connections. The electric feeding therefore occurs, on the one hand, directly via the carrier element and, on the other hand, via an electric cable, for example, such that the light emitting diode is connected to the other, free connection pole. The carrier element, which has a relatively large volume, can therefore quickly accept and dissipate the heat developed by the at least one light emitting diode. The heat in points generated at the LED is immediately dissipated to the carrier element, which has a good heat absorption capacity by the comparatively great volume in connection to good heat conductivity. The fact that the carrier is embodied rod-shaped also contributes thereto, and that carrier extends from the installation site of the LED as far as possible to the rear part of the handle, which is embodied with a dissipation and cooling surface sufficient for cooling the LED. The carrier element can here extend, perhaps originating at the coupling site between the probe part and the handle, to the rear part of the handle. The rear area of the handle is therefore well utilized. Here, the carrier element is thermally connected to housing parts and/or installation parts of the handle and the probe part, if applicable, such that the volume and/or the surface of all thermally contacted elements can serve to dissipate head and cool the LED. A coupling with bayonet-like engaging coupling parts is arranged between the handle and the probe part, with the coupling parts being in thermal contact to the LED carrier element via a holding plate and the heat bridging part such that these parts also contribute to the dissipation of heat.

When using and utilizing these cooling and dissipating measures, a continuous operation of the lighting is even possible under disadvantageous environmental conditions, i.e., increased environmental temperature.

Experiments have shown that by these measures the overall heating of the handle of the endoscope remains below the permissible limit and particularly below 50° C. even when one or more LEDs of high power are used. In conventional operating terms with a continuously active LED the heating remains below this temperature. The above-described heat dissipation and radiation measures may also include a certain heat radiation towards the environment via the handle itself.

Here, the carrier element comprises copper or aluminum or a material exhibiting similarly sound heat conducting features.

As already mentioned, the installation parts of the handle can be used for heat dissipation for the heat created by the LED and transferred to the carrier element. For this purpose, the holder for the carrier element and a lens cartridge can be embodied as a heat-bridging part such that the lens cartridge can be in a thermal contact with the carrier element.

Furthermore, the lens cartridge can be connected coaxially to a camera socket so that both parts serve for heat dissipation. It is particularly advantageous when the camera socket is in thermal contact, particularly via a rear-side holding socket, with an external cap nut or a similar end or screw part.

The part located externally at the rear end of the handle results in a good heat dissipation of the heat conducted from the LED via the installation parts to the outside environmental air, with this part of the handle being located practically outside the holding area when the handle is held.

A particularly effective heat dissipation and radiation towards the outside results when one of the coupling parts is embodied as a locking part with an external, latch-like appendage as the handle for rotating the locking part. This latch-like appendage itself practically forms a cooling tab, in addition to the heat-dissipating locking part, which causes particular good heat dissipation towards the environment by its surface positioned outside the interior of the housing.

The threaded parts or the like at the rear end of the handle and the coupling parts with their latch-shaped closing part at the other end usually comprise metal, thus providing good head dissipation.

Additional embodiments of the invention are disclosed in the other sub-claims.

BRIEF DESCRIPTION OF THE DRAWINGS

In the following, the invention is described in greater detail using the drawings.

Shown are:

FIG. 1 is a perspective view of an endoscope with a handle and a probe part, which are shown separated from each other, FIG. 2 is a longitudinal cross-sectional view of a handle, FIG. 3 is a perspective view of a carrier element and a light emitting diode connected thereto, FIG. 4 is a perspective view of a probe part and a handle shown in part, separated from the probe part, FIG. 5 is a perspective view of a handle with a view to the end of the coupling in a closed locking part.

DETAILED DESCRIPTION OF THE PREFERRED EMBODIMENTS

An endoscope 1 shown in FIG. 1 is essentially comprised of a handle 2 as well as a probe part 3 that can be connected thereto. These two parts 2 and 3 can be connected to each other via a coupling 7. A rotational locking part 5 is provided at the handle 2 and a plate-shaped coupling counterpart 4 at the probe part 3, which engage each other in the locked position like a bayonet.

An illumination system with a light emitting diode 6 (cf. FIGS. 2, 3, and 5) is arranged in the handle 2. The light created by the light emitting diode 6 is guided, when the probe part 3 is coupled, in a light conductor 8 located in the probe part and via said part to the distal end of the actual probe 9.

Furthermore, a video system with a camera 10 and a lens cartridge 11, connected upstream, is provided in the handle 2.

The light emitting diode 6 of the illumination system is connected to a carrier element 12 comprising a heat conducting material, with the LED being thermally coupled directly to the carrier element. Here, the carrier element forms a stable mounting and a heat dissipating body.

The carrier element 12, which is shown in a perspective together with the light emitting diode 6 in FIG. 3, may comprise copper or aluminum and is embodied rod-shaped in the exemplary embodiment. It extends from the installation site of the light emitting diode 6 near the coupling 7 to a rear section of the handle 2. The light emitting diode 6 is connected to the distal facial end of the carrier element 12, particularly soldered to said face. Here, an electric connection pole of the light emitting diode 6 is connected to the carrier element 12, while the other electric connection pole remains clear for a connecting cable.

In the exemplary embodiment, the carrier element 12 is provided with a stop-forming recess 13, into which area the light emitting diode 6 protrudes with its one, free electric connection pole. The electric feed occurs therefore, on the one hand, directly via the carrier element 12 and, on the other hand, via an electric cable 14 (cf. FIG. 2), which is connected to the other, free connection pole of the light emitting diode 6. Via this cable 14 as well as another electric cable 14*a*, connected to the carrier element 12 at the rear, the power feed occurs to the light emitting diode 6. The two cables 14, 14*a* are guided out of the handle 2 at the rear through a cable screw connection together with other electric cables, not shown here, leading to the installed camera 10.

In FIG. 2 and particularly FIG. 3 it is clearly discernible that the carrier element 12 is provided with a longitudinal groove 15, in which the electric cable 14 is guided.

The carrier element 12 has a relatively large volume, so that the heat created by the light emitting diode 6 can be quickly absorbed and dissipated. Depending on the power of the light emitting diode 6 and the size of the carrier element 12, the heat dissipation that can be achieved here may be sufficient, at least for shorter operating periods. However, it is preferred for the carrier element 12 to be provided with housing parts and/or installation parts of the handle that are in a thermal contact and which dissipate and/or guide off the heat developing by the light emitting diode 6.

This heat dissipation is particularly beneficial when the external housing 23 of the handle 2 comprises plastic, as common, and thus shows reduced heat conductivity. This is desirable, on the other hand, because the handle is held manually during the operation of the endoscope and thus the exterior of the housing should heat as little as possible in the holding area.

The heat developing inside the handle 2, particularly by the light emitting diode 6, should therefore only be transferred to the external holding area of the handle 2 to a minor extent and instead is carried to locations not coming into contact with the hand holding the handle.

The rod-shaped carrier element 12 is supported to be movable in the longitudinal direction and is supported at the rear by a spring 24. When coupling the probe part 3, the off-set fiber-optic pin 25 of the probe part presses against the light emitting diode 6 located in the handle 2, and the movable illumination unit with the LED 6 and the carrier element 12 deflect against the spring force in a tubular guiding part 22. In the coupled position, the illumination unit is constantly pressed by the spring force against the fiber-optic pin 25 such that an optimal light transfer is given. Additionally, heat is dissipated from the LED via this contact site to the probe part 3.

Finally, by the spring-loaded support of the carrier element 24 it is ensured that, on the one hand, the light transfer end surfaces of the ocular lens system and, on the other hand, of the image conductor bundle located in the pin 26 of the probe 3 are precisely allocated to each other, and/or are in close contact against each other.

The carrier element 12 is supported in a holder 16, which is embodied essentially plate-shaped and has a bore for the carrier element 12 as well as a bore arranged next to it for the lens cartridge 11. This holder 16 forms a heat bridging part, via which the heat is transferred from the carrier element 12 to the lens cartridge 11.

Coaxially in reference to the lens cartridge 11, a camera socket 17 is arranged abutting at the rear, which also is in a thermal contact to the lens cartridge 11 and dissipates the developing heat to the rear end of the handle 2. Finally, a metal cap nut 18 is arranged at the rear of the handle 2, which is connected via a similarly metallic fastening socket 19 to the camera socket 17.

In this way, starting at the light emitting diode 6, a thermally conducting connection is formed to the cap nut 18 screwed to the handle 2 located at the outside, via the carrier element 12, the fastener 16, the lens cartridge 11, the camera socket 17, and the fastening socket 19. Here, heat dissipation towards the environment occurs via the cap nut 18, with this cap nut 18 being located outside the contact area when holding the handle 2.

The lens cartridge 11 is connected with its distal end to a holding plate 20 and this holding plate 20 in turn is connected to the externally located locking part 5 allocated to the coupling 7. This locking part 5 is pivotal between an open position (FIG. 4) and a closed position (FIG. 5) and is provided with an external, tab-shaped appendage 21 as a handle for rotating the locking part. The locking part 5 is generally made from metal, so that good heat dissipation to the outside is possible via this part as well.

With its free stop, smaller in diameter, the off-set fiber-optic pin 25 of the probe part 3 engages in the coupling position the tubular guidance part 22 of the handle 2 and the circular facial face of the guidance part 22 contacts the pin 25 having a stop with a greater diameter. This separation site is positioned such that its tab-shaped appendage 21 snaps over the locking part 5 and bridges it in the closing position. The appendage therefore forms another heat bridge via which heat can be conducted and dissipated from the guidance part 22 to the pin 25 and thus to the probe part 3.

In the coupling position of the handle to the probe part 3, the coupling counterpart 4 of the probe part 3 allocated to the coupling 7 engages the locking part 5 of the handle 2, with a connection being formed engaging like a bayonet. Here, the coupling counterpart 4 of the probe part 3 thermally contacts the locking part 5 such that this part too contributes to the heat dissipation. The tab-like appendage 21 of the locking part 5 snaps over a sheath-like guidance part 22 of the illumination system in the locked position, with the carrier element 12 for the light emitting diode 6 being supported in this guidance part. This results in additional heat dissipation via the guidance part 22 to the appendage 21 of the locking part 5 and thus via said part, too.

The installation parts of the endoscope used for heat transfer and heat dissipation comprise sound heat conducting materials, particularly metal.

The measures according to the invention with regard to heat conductivity and heat dissipation of heat created by the high-power light emitting diode or diodes can be realized in compact and even miniaturized endoscopes.

The invention claimed is:

1. An endoscope comprising a handle (2) and a probe part (3) which can be connected thereto, an illumination system having at least one light emitting diode (5) and a video system with an image receiver arranged in the handle (2), a carrier element (12) arranged inside the handle (2) is provided for the at least one light diode (6) comprising a heat dissipating material, to which the light diode (6) is directly connected, and with the carrier element (12) is in a thermal contact with at least one of housing parts or installation parts of the handle (2) and the probe part (3), the carrier element (12) is rod-shaped and extends from an installation site of the light emitting diode (6) towards a proximal end of the handle (2) to such an extent that a sufficient dissipation and cooling surface is formed for cooling the light emitting diode (6), at least one of a volume or a surface of all thermally contacted elements serve for heat dissipation and cooling of the at least one light emitting diode (6), the at least one light emitting diode (6) has one pole of its electric connections connected to the carrier element (12), a holder (16) is in a thermal contact to the carrier element (12) and a lens cartridge (11) and acts as a heat bridging part, and a coupling (7) is arranged between the handle (2) and the probe part (3), which includes bayonet-like engaging coupling parts (4, 5), the coupling parts (4, 5) are in thermal contact with the carrier element (12) of the light emitting diode via a holding plate (20) and the holder (16) as a heat bridging part.

2. An endoscope according to claim 1, wherein the carrier element (12) for the light emitting diode (6) comprises copper or aluminum or a material of similarly good heat conductivity.

3. An endoscope according to claim 1, wherein the lens cartridge (11) is coaxially connected to a camera socket (17) and both parts serve to dissipate heat.

4. An endoscope according to claim 3, wherein the camera socket (17) is thermally connected via a rear holding socket (19) to an external cap nut (18) or threaded part.

5. An endoscope according to claim 1, wherein one of the coupling parts is embodied as a rotational locking part (5) having an external, tab-like appendage (21) as a handle for rotating the locking part (5).

6. An endoscope according to claim 5, wherein in that in a closed position of the locking part (5), the tab-like appendage (21) bridges engaging parts of the handle (2) and the probe part (3) and thermally couples, a tubular guidance part (22) of the handle (2) for supporting the carrier element (12) and a fiber-optic pin (25) of the probe part (3).

\* \* \* \* \*